US012586687B2

(12) United States Patent
Hotlani

(10) Patent No.: US 12,586,687 B2
(45) Date of Patent: Mar. 24, 2026

(54) SYSTEMS AND METHODS OF DEDUPLICATING DATA COLLECTED BY AN IMPLANTABLE MEDICAL DEVICE

(71) Applicant: THE ALFRED E. MANN FOUNDATION FOR SCIENTIFIC RESEARCH, Valencia, CA (US)

(72) Inventor: Hitesh Hotlani, Santa Clarita, CA (US)

(73) Assignee: THE ALFRED E. MANN FOUNDATION FOR SCIENTIFIC RESEARCH, Valencia, CA (US)

( * ) Notice: Subject to any disclaimer, the term of this patent is extended or adjusted under 35 U.S.C. 154(b) by 278 days.

(21) Appl. No.: 18/462,156

(22) Filed: Sep. 6, 2023

(65) Prior Publication Data

US 2024/0079147 A1 Mar. 7, 2024

Related U.S. Application Data

(60) Provisional application No. 63/404,453, filed on Sep. 7, 2022.

(51) Int. Cl.
*G16H 50/70* (2018.01)
*A61N 1/02* (2006.01)
*A61N 1/372* (2006.01)
*G16H 40/67* (2018.01)

(52) U.S. Cl.
CPC ............ *G16H 50/70* (2018.01); *A61N 1/025* (2013.01); *A61N 1/37211* (2013.01); *G16H 40/67* (2018.01)

(58) Field of Classification Search
None
See application file for complete search history.

(56) References Cited

U.S. PATENT DOCUMENTS

| | | | |
|---|---|---|---|
| 2016/0004820 A1* | 1/2016 | Moore | G16H 15/00 |
| | | | 705/3 |
| 2018/0078770 A1 | 3/2018 | Rickert et al. | |
| 2021/0316151 A1 | 10/2021 | Andersen | |

FOREIGN PATENT DOCUMENTS

| | | |
|---|---|---|
| CN | 113438198 A | 9/2021 |
| WO | WO 2019/067630 A1 | 4/2019 |

OTHER PUBLICATIONS

International Search Report for PCT/US2023/032093 dated Jan. 2, 2024, 4 pages.

* cited by examiner

*Primary Examiner* — Deborah L Malamud
(74) *Attorney, Agent, or Firm* — Lewis Roca Rothgerber Christie LLP

(57) ABSTRACT

An implantable medical device and a method of deduplicating data collected by the implantable medical device are provided. The method includes storing data, captured by the implantable medical device, in a non-volatile memory device of the implantable medical device, assigning a unique number, generated from a random number generator or counter, to each data block of the data, and deduplicating the data by deleting at least one of two or more data blocks that are associated with the same unique number.

5 Claims, 9 Drawing Sheets

200

START

STORE DATA CAPTURED BY THE IPG
210

ASSIGN A UNIQUE IDENTIFIER TO
EACH DATA BLOCK
220

TRANSMIT THE DATA INCLUDING THE
UNIQUE IDENTIFIER ASSOCIATED WITH
EACH DATA BLOCK TO A SERVER
230

DEDUPLICATE THE DATA
AT THE SERVER
240

END

SYSTEMS AND METHODS OF DEDUPLICATING DATA COLLECTED BY AN IMPLANTABLE MEDICAL DEVICE

CROSS-REFERENCE TO RELATED APPLICATION(S)

The present application claims priority to and the benefit of U.S. Provisional Application No. 63/404,453, filed Sep. 7, 2022, the entire contents of which are incorporated herein by reference.

BACKGROUND

1. Field

The present disclosure relates to various systems and methods of deduplicating data.

2. Description of the Related Art

Implantable pulse generators (IPGs) are used for a variety of therapeutic treatments in a patient, such as neurostimulation, cardiac stimulation, and spinal cord stimulation. IPGs store a variety of data regarding the patient and the therapeutic settings of the IPG. Data storage capacity on the IPG is limited and therefore periodic reads of the data from the IPG typically occur to prevent the loss of data. Clinician programmer (CP) and patient remote (PR) devices are commonly used to read the data off of the IPG and then upload the data to the "cloud" or a server, where remote monitoring of the data occurs. The CP and PR devices may be useful for follow-up patient visits when historical data cannot be downloaded or otherwise accessed from the cloud or the server.

The IPG commonly tracks the status of data (e.g., not read, read, or uploaded). Based on the use case requirement, the CP device and/or the PR device can either read all of the data or only read new data. Accordingly, the IPG may keep of the data that can be stored based on its available internal memory size and will selectively send data to the CP device and/or the PR device. Alternatively, data could be deleted from the IPG once it has been uploaded to the server and upload confirmation has been received by the IPG.

In some cases, however, data could be read from the IPG by the CP device or the PR device but not uploaded to the cloud or the server (e.g., due to loss of internet connectivity), which may result in some data being read by both the CP device and the PR device. Reading data from both the CP device and the PR device may result in data duplication on the cloud or the server. Data duplication on the cloud or the server may result in the IPG being programmed with inadvertently incorrect therapy settings, because the data presented to the cloud or the server may be skewed due to duplication of certain data.

Furthermore, applying a timestamp alone to the data on the IPG is insufficient to enable deduplication of the data, because the IPG only stores the timestamp up to a granularity of a second and data is recorded more frequently than every second. Thus, applying a timestamp alone is not unique enough to enable deduplication of the data without inadvertently deleting data that is not actually duplicated.

SUMMARY

The present disclosure relates to various embodiments of a method of deduplicating data collected by an implantable medical device, such as an implantable pulse generator. In one embodiment, the method includes storing data, captured by the implantable medical device, in a non-volatile memory device of the implantable medical device. The method also includes assigning a unique number, generated from a random number generator or a counter, to each data block of the data, and deduplicating the data by deleting at least one of two or more data blocks being associated with the same unique number. The random number generator may be a 4-byte random number generator, and the counter may be a 4-byte counter.

In another embodiment, the method includes storing data, captured by the implantable medical device, in a non-volatile memory device of the implantable medical device, assigning a unique identification, including a combination of a datetime stamp and a counter, to each data block of the data, and deduplicating the data by deleting at least one of two or more data blocks being associated with the same unique identification. The counter may be a 2-byte counter.

In a further embodiment, the method includes storing data, captured by the implantable medical device, in a non-volatile memory device of the implantable medical device assigning a unique identification, including a combination of a datetime stamp and number generated from a counter, to each data block stored in the non-volatile memory device, and deduplicating the data by deleting at least one of two or more data blocks being associated with the same unique identification. The counter may be a 1-byte counter.

The present disclosure also relates to various embodiments of an implantable medical device In one embodiment, the implantable medical device includes a processor, a communications device (circuit) configured to communicate with a patient remote device and a clinician programmer device, a power supply, and a memory device (circuit) having computer-readable instructions stored therein which, when executed by the processor, cause the implantable medical device to store a number of data blocks in the memory device, and assign a unique identifier to each data block of the number of data blocks.

This summary is provided to introduce a selection of features and concepts of embodiments of the present disclosure that are further described below in the detailed description. This summary is not intended to identify key or essential features of the claimed subject matter, nor is it intended to be used in limiting the scope of the claimed subject matter. One or more of the described features may be combined with one or more other described features to provide a workable system or method of deduplicating data.

BRIEF DESCRIPTION OF THE DRAWINGS

The features and advantages of embodiments of the present disclosure will be better understood by reference to the following detailed description when considered in conjunction with the drawings. The drawings are not necessarily drawn to scale.

DETAILED DESCRIPTION

Figure 1A:
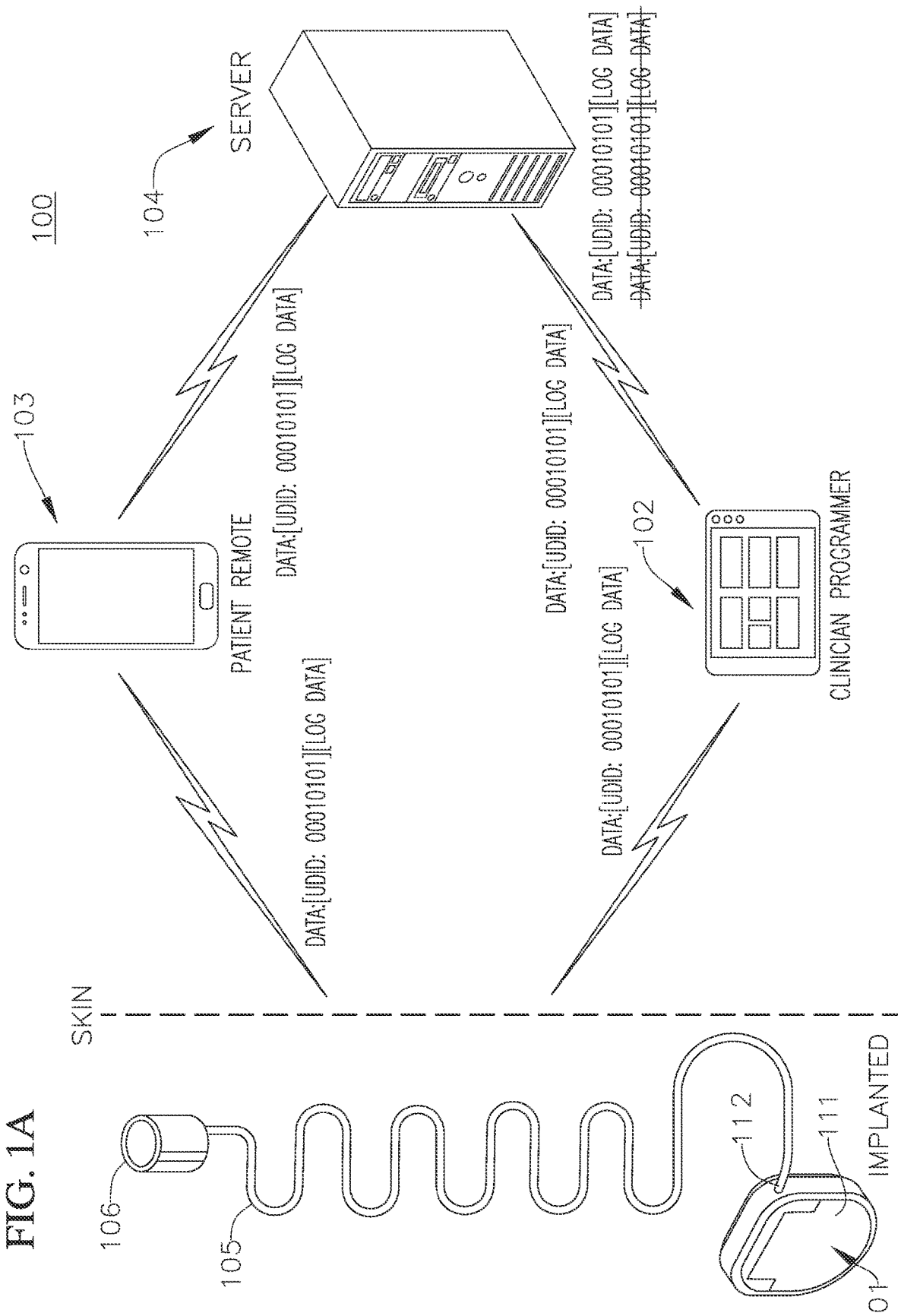
FIG. 1A is a schematic view of a therapeutic system including an implantable pulse generator (IPG), a clinician programmer (CP) device, a patient remote (PR) device, and a server for deduplicating data captured by the IPG according to one embodiment of the present disclosure.

Aspects of the present disclosure relate to various embodiments of a system and a method for deduplicating data collected or otherwise obtained from an implantable medical device, such as an implantable pulse generator (IPG), implanted in a patient. In one or more embodiments, the methods of the present disclosure are configured to deduplicate data when the rate at which data is stored on the implantable medical device (e.g., the IPG) is greater than the resolution of the timestamp that the implantable medical device (e.g., the IPG) stores, because in such a case the timestamp alone is not unique enough to enable deduplication of the data without inadvertently deleting data that is not actually duplicated.

In one or more embodiments, the methods of the present disclosure may assign a unique number, generated from a random number generator or a counter, to each block of data stored in the implantable medical device (e.g., the IPG). In one example, the unique number may be generated from a 4-byte random number generator or a 4-byte counter, which would allow for more than 4 billion unique data entries to be stored in the implantable medical device (e.g., the IPG).

In one or more embodiments, the methods of the present disclosure may assign a unique identification, including a combination of a datetime stamp and a number generated by a counter (e.g., a 2-byte counter), to each block of data stored in the implantable medical device (e.g., the IPG). In one or more embodiments, the methods of the present disclosure may assign a unique identification, including a combination of a datetime stamp and a number generated by a counter (e.g., a 1-byte counter), for each block of data stored in the implantable medical device (e.g., the IPG) in a one-second time interval. Each of these methods results in a unique identifier being assigned to each data block stored in the implantable medical device (e.g., the IPG), which may then be utilized by the server to delete at least one data block when two or more data blocks are associated with the same unique identifier.

The terminology utilized herein is for the purpose of describing particular embodiments only and is not intended to be limiting of the present disclosure. As utilized herein, the singular forms "a", "an" and "the" are intended to include the plural forms as well, unless the context clearly indicates otherwise. As utilized herein, the term "and/or" includes any and all combinations of one or more of the associated listed items.

It will be understood that, although the terms "first", "second", "third", etc., may be utilized herein to describe one or more suitable elements, components, regions, and/or sections, these elements, components, regions, and/or sections should not be limited by these terms. These terms are only utilized to distinguish one element, component, region, layer or section from another element, component, region, layer or section. Thus, a first element, component, region, or section discussed could be termed a second element, component, region, or section, without departing from the spirit and scope of the present disclosure.

It will be understood that when an element is referred to as being "on", "connected to", "coupled to", or "adjacent to" another element, it can be directly on, connected to, coupled to, or adjacent to the other element, or one or more intervening element(s) may be present. In contrast, when an element is referred to as being "directly on," "directly connected to", "directly coupled to", or "immediately adjacent to" another element, there are no intervening elements present.

As utilized herein, the term "substantially" and similar terms are utilized as terms of approximation and not as terms of degree, and are intended to account for the inherent deviations in measured or calculated values that would be recognized by those of ordinary skill in the art. Also, the terms "about," "approximately," and similar terms, when utilized herein in connection with a numerical value or a numerical range, are inclusive of the stated value and refer to within an acceptable range of deviation for the particular value as determined by one of ordinary skill in the art, considering the measurement in question and the error associated with measurement of the particular quantity (e.g., the limitations of the measurement system).

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Example embodiments of the present disclosure will now be described with reference to the accompanying drawings. In the drawings, the same or similar reference numerals refer to the same or similar elements throughout. As utilized herein, the utilize of the term "may," when describing embodiments of the present disclosure, refers to "one or more embodiments of the present disclosure."

FIG. 1A is a schematic view of a therapeutic system 100 according to one embodiment of the present disclosure. In the illustrated embodiment, the system 100 includes an implantable medical device (e.g., an implantable pulse generator (IPG)) 101 implanted in a patient, a clinician programmer (CP) device 102 electronically coupled to (i.e., in wireless communication with) the IPG 101, a patient remote (PR) device 103 electronically coupled to (i.e., in wireless communication with) the IPG 101, and a server 104 electronically coupled to (i.e., in wireless communication with) the CP device 102 and the PR device 103. The system 100 also includes a plurality of electrical leads 105 connected to the IPG 101. Each of the electrical leads 105 includes an electrode 106 (e.g., at a distal end of the electrical lead 105) to periodically deliver an electric current pulse for a variety of therapeutic treatments for the patient, such as neurostimulation, cardiac stimulation, and/or spinal cord stimulation. The IPG 101 and the electrical leads 105 may be implanted in any suitable locations in the patient depending on the therapeutic treatment delivered by the system 100. For example, the IPG 101 may be implanted in a subcutaneous pocket in the upper chest of the patient, and the electrical leads 105 may extend from the IPG 101 through the superior vena cava such that the electrodes 106 are connected to the myocardium of the patient's heart.

Figure 1B:
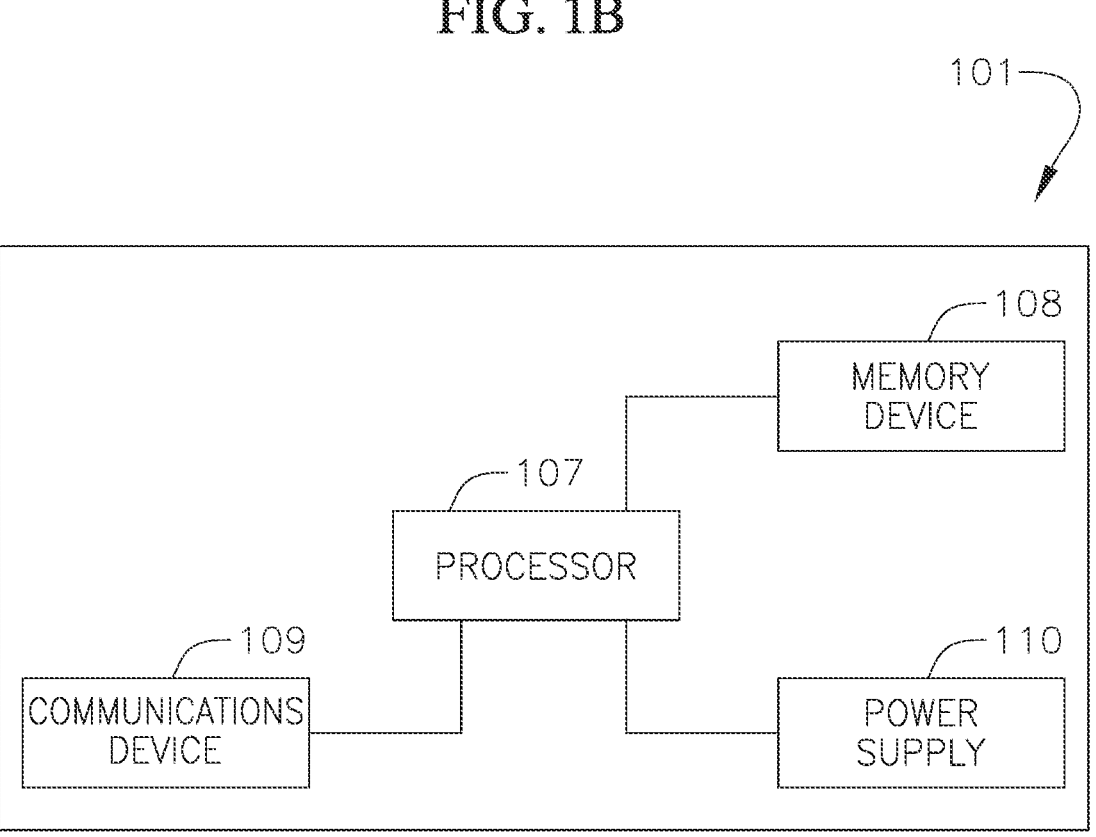
FIG. 1B is a schematic block diagram of the IPG according to the embodiment illustrated in FIG. 1A.

In the embodiment illustrated in FIG. 1B, the implantable medical device (e.g., the IPG) 101 includes a processor 107, a non-volatile memory device 108 (e.g., flash memory, or read-only memory (ROM), such as programmable read-only memory (PROM) or erasable programmable read-only memory (EPROM)), a communications device (circuit) 109 (e.g., a receiver and a transmitter, or a transceiver), and a power supply 110 (e.g., a primary battery or an inductively chargeable rechargeable battery). The communications device 109 provides wireless communication links through the skin of the patient to the CP device 102 and the PR device 103. Wireless links may include Bluetooth™, Bluetooth Low Energy or other protocols with suitable authentication and encryption to protect patient data. In one or more embodiments, the non-volatile memory device (circuit) 108, the communications device 109, and the power supply 110 are in communication with each other over the processor 107. Additionally, in the illustrated embodiment, the processor 107, the non-volatile memory device 108, the communications device 109, and the power supply 110 are housed in a housing or a case 111, and proximal end portions of the electrical leads 105 extend through opening(s) 112 in the housing 111 and are connected to the power supply 110.

The memory device 108 of the IPG 101 is configured to store various data about the patient (e.g., physiological data regarding the patient, therapeutic parameters or settings of the IPG 101, and/or any other relevant data), and the CP device 102 and the PR device 103 are each configured to periodically read and transmit the data stored on the memory device 108 of the IPG 101 to the server 104, which enables remote monitoring of the system 100.

In one or more embodiments, the memory device 108 of the IPG 101 includes instructions (e.g., computer-readable code) stored therein, which, when executed by the processor 107, cause the IPG 101 to generate and assign a unique identifier to each data block that is stored in the memory device 108 of the IPG 101. Assigning a unique identifier to each data block as it is saved on the memory device 108 enables the data received by the server 104 from the CP device 102 and the PR device 103 to be deduplicated (e.g., if the same data is sent to the server 104 both by the CP device 102 and the PR device 103).

In the illustrated embodiment, the instructions stored in the memory device 108 include a random number generator (or a pseudo-random number generator (PRNG)) or a counter. In one or more embodiments, the random number generator or the PRNG may be a 4-byte random number generator or a 4-byte PRNG, although in one or more embodiments, the random or pseudo-random number generator may be 5-byte or greater random or pseudo-random number generator. In one or more embodiments, the counter may be a 4-byte counter, although in one or more embodiments, the counter may be 5-byte or greater counter. In one or more embodiments, the 4-byte random number generator includes a recursive algorithm, and the processor 107 is configured to supply the current datetime as the input (i.e., the "seed") to the recursive algorithm to generate a random number or a pseudo-random number. In one or more embodiments, any other seed may be utilized. Accordingly, in one or more embodiments in which the random number generator or the counter are a 4-byte random number generator or a 4-byte counter, the instructions stored in the memory device 108, when executed by the processor 107, are configured to generate and assign over 4 billion (i.e., $2^{32}$=approximately (about) 4.29 billion) unique values to the data blocks as they are stored in the memory device 108, which enables data blocks that have been assigned the same unique value to be deduplicated without risk of inadvertently deleting non-duplicated data. In one or more embodiments, the random number generator (or the PRNG) or the counter may have any other suitable number of bytes, such as a 5-bytes or more, depending upon the number of unique data blocks that are stored in the memory device 108.

Figure 2:
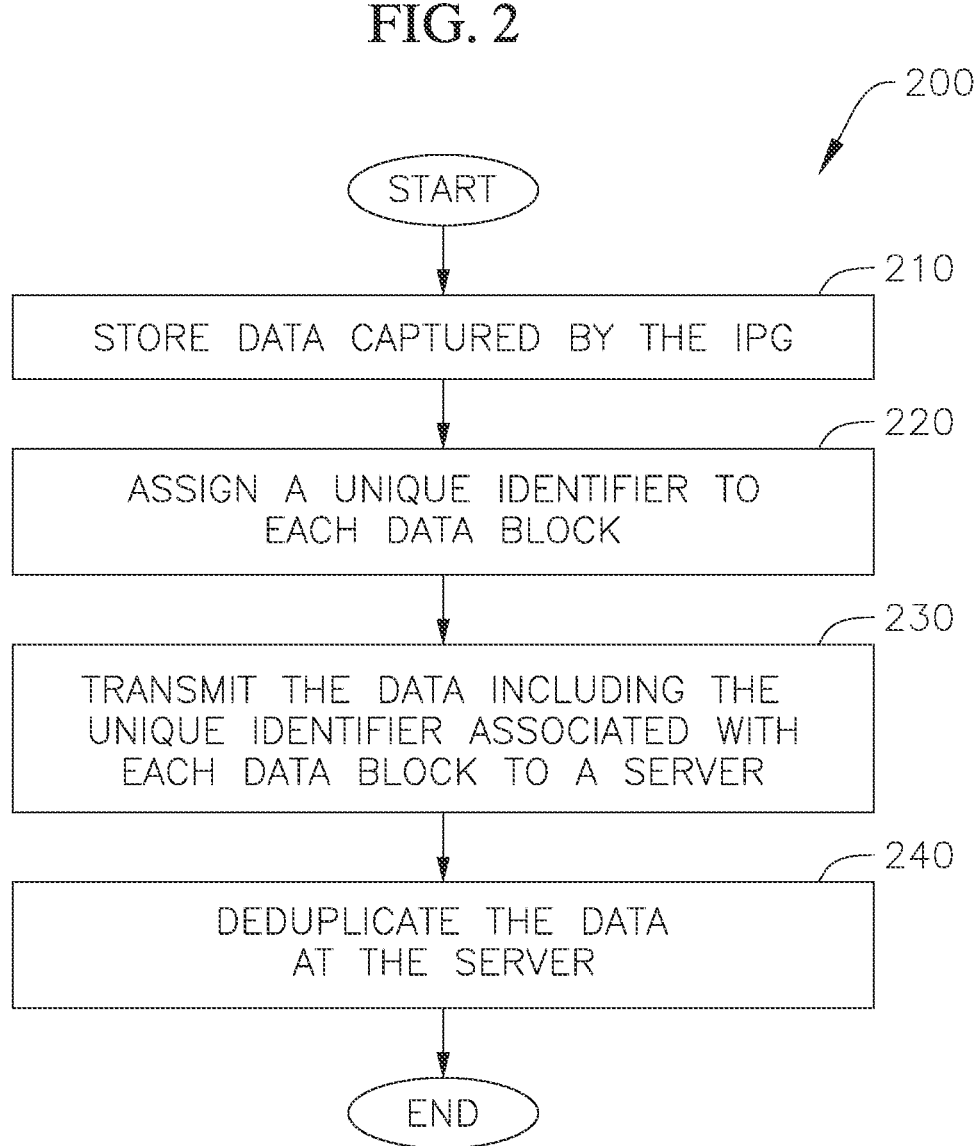
FIG. 2 is a flowchart illustrating tasks of a method of deduplicating data utilizing the therapeutic system of FIGS. 1A-1B according to one embodiment of the present disclosure.

FIG. 2 is a flowchart illustrating tasks of a method 200 of deduplicating data on the system 100 disclosed in FIGS. 1A-1B. In the illustrated embodiment, the method 200 includes a task 210 of storing data, captured or collected by the implantable medical device (e.g., the IPG) 101, in the non-volatile memory 108 of the IPG 101. The data captured or collected by the IPG 101 in task 210 may include physiological data regarding the patient, therapeutic parameters or settings of the IPG 201, and/or any other relevant data.

In the illustrated embodiment, the method 200 also includes a task 220 of assigning a unique identifier (e.g., a unique number or value) to each block of data that was captured or collected by the IPG 101 in task 210, and storing the unique identifier with the associated data block stored in task 210. The unique identifier assigned in task 220 may be a number generated by a random number generator (e.g., a 4-byte or greater random number generator) or by a counter (e.g., a 4-byte or greater counter). In one or more embodiments in which the unique number is generated by a 4-byte random number generator, the task 220 may include supplying a recursive algorithm with the current datetime as the "seed" (i.e., the base value supplied as an input to the recursive algorithm). The 4-byte random number generator and the 4-byte counter are configured to generate over 4 billion (i.e., $2^{32}$=approximately 4.29 billion) unique values, and thus the IPG 201 may store data having over 4 billion data blocks that are uniquely identified according to one embodiment of the present disclosure.

In the illustrated embodiment, the method 200 also includes a task 230 of transmitting the data (and the associated unique identifier assigned in task 220 to each data block) from the IPG 101 to the server 104. In one or more embodiments, the data (and the associated unique identifier) may be transmitted to the server 104 by the CP device 102 and/or the PR device 103. In one or more embodiments, in task 230, the data (and the associated unique identifier) stored in the non-volatile memory device 108 on the IPG 101 may be read by both the CP device 102 and the PR device 103 and then transmitted by both the CP device 102 and the PR device 103 to the server 104.

In the illustrated embodiment, the method 200 also includes a task 240 of deduplicating the data received by the server 104 in task 230 by deleting at least one of two or more data blocks that are associated with the same unique identifier (e.g., the same unique number) that was assigned to the data blocks in task 220. For instance, in a use case in which both the CP device 102 and the PR device 103 read and transmit the data from the IPG 101 to the server 104 in task 230, two or more data blocks associated with the same unique identifier (e.g., the same unique number generated by the 4-byte random number generator or the 4-byte counter) may have been transmitted to the server 104 in task 230. However, because a unique identifier (e.g., a unique number) is assigned to each of the data blocks stored in the non-volatile memory 108 of the IPG 101 in task 220, excess data blocks that are associated with the same unique identifier may be safely deleted by the server 104 without inadvertently deleting non-duplicative data.

Figure 3A:
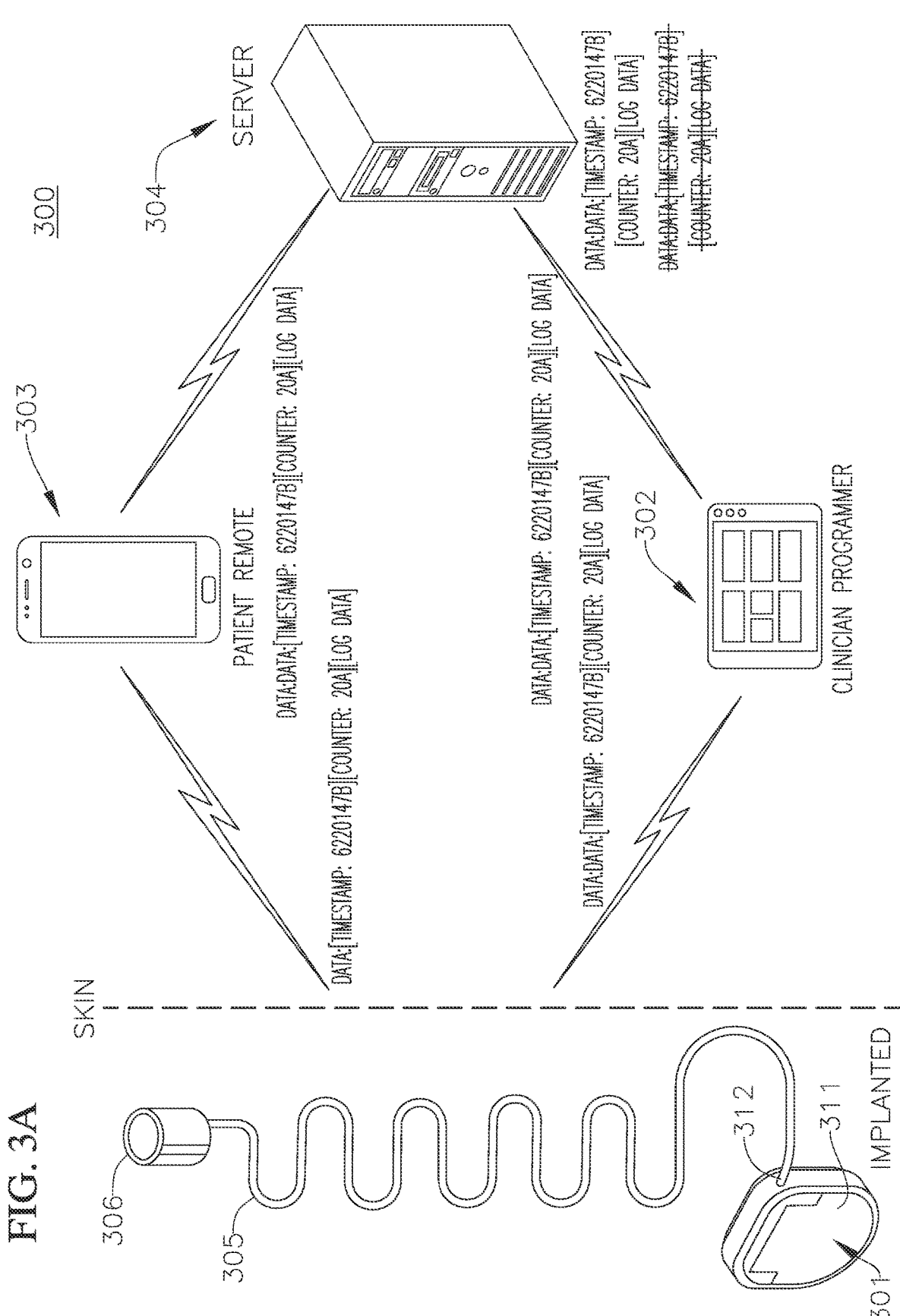
FIG. 3A is a schematic view of a system including an implantable pulse generator (IPG), a clinician programmer (CP) device, a patient remote (PR) device, and a server for deduplicating data captured by the IPG according to another embodiment of the present disclosure.

FIG. 3A is a schematic view of a therapeutic system 300 according to one embodiment of the present disclosure. In the illustrated embodiment, the system 300 includes an implantable medical device (e.g., an implantable pulse generator (IPG)) 301 implanted in a patient, a clinician programmer (CP) device 302 electronically coupled to (i.e., in wireless communication with) the IPG 301, a patient remote (PR) device 303 electronically coupled to (i.e., in wireless communication with) the IPG 301, and a server 304 electronically coupled to (i.e., in wireless communication with) the CP device 302 and the PR device 303. The system 300 also includes a plurality of electrical leads 305 connected to the IPG 301. Each of the electrical leads 305 an electrode 306 to periodically deliver an electric current pulse for a variety of therapeutic treatments for the patient, such as neurostimulation, cardiac stimulation, and/or spinal cord stimulation. The IPG 301 and the electrical leads 305 may be implanted in any suitable locations in the patient depending on the therapeutic treatment delivered by the system 300.

Figure 3B:
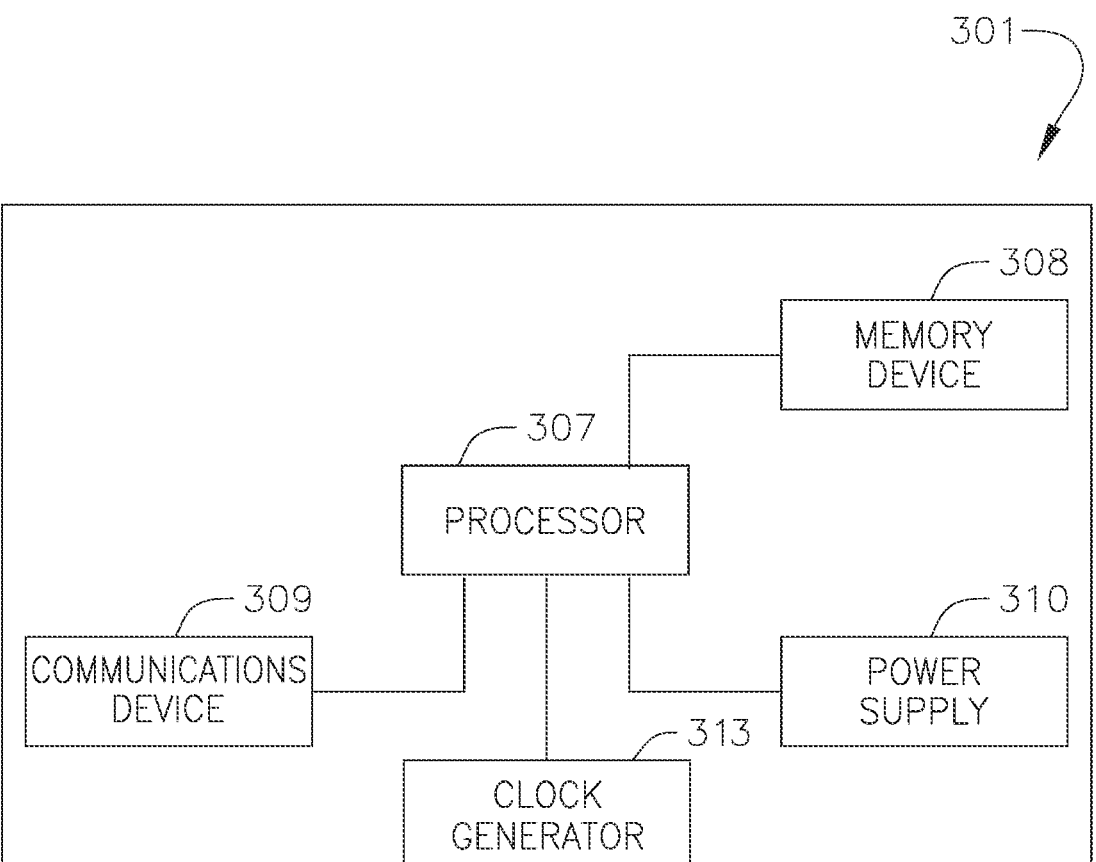
FIG. 3B is a schematic view of the IPG according to the embodiment illustrated in FIG. 3A.

In the embodiment illustrated in FIG. 3B, the implantable medical device (e.g., the IPG) 301 includes a processor 307, a non-volatile memory device 308 (e.g., flash memory, or read-only memory (ROM), such as programmable read-only memory (PROM) or erasable programmable read-only memory (EPROM)), a communications device 309 (e.g., a receiver and a transmitter, or a transceiver), and a power supply 310 (e.g., a primary battery or an inductively chargeable rechargeable battery). The communications device 309 provides wireless communication links through the skin of the patient to the CP device 302 and the PR device 303. Wireless links may include Bluetooth™, Bluetooth Low Energy or other protocols with suitable authentication and encryption to protect patient data. In one or more embodiments, the non-volatile memory device 308, the communications device 309, and the power supply 310 are in communication with each other over the processor 307. Additionally, in the illustrated embodiment, the processor 307, the non-volatile memory device 308, the communications device 309, and the power supply 310 are housed in a housing or a case 311, and proximal end portions of the electrical leads 305 extend through opening(s) 312 in the housing 311 and are connected to the power supply 310.

In the illustrated embodiment, the IPG 301 also includes a clock generator 313 (e.g., an oscillator, such as a quartz crystal oscillator, a polycrystalline ceramic oscillator, or other piezoelectric oscillator) configured to generate and provide a clock signal to coordinate write operations to the memory device 308. In one or more embodiments, the clock generator 313 may have a 32 KHz frequency.

The memory device 308 of the IPG 301 is configured to store various data about the patient (e.g., physiological data regarding the patient, therapeutic parameters or settings of the IPG 301, and/or any other relevant data), and the CP device 302 and the PR device 303 are each configured to periodically read and transmit the data stored on the memory device 308 of the IPG 301 to the server 304, which enables remote monitoring of the system 300.

In one or more embodiments, the memory device 308 of the IPG 301 includes instructions (e.g., computer-readable code) stored therein, which, when executed by the processor 307, cause the IPG 301 to generate and assign a unique identifier to each data block that is stored in the memory device 308 of the IPG 301. Assigning a unique identifier to each data block as it is saved on the memory device 308 enables the data received by the server 304 from the CP device 302 and the PR device 303 to be deduplicated (e.g., if the same data is sent to the server 304 both by the CP device 302 and the PR device 303).

In the illustrated embodiment, the unique identifier is a combination of a value (e.g., a number) and a datetime stamp. In the illustrated embodiments, the instructions stored in the memory device 308 include a 2-byte counter configured to generate 65,536 (i.e., $2^{16}$) unique values. In one or more embodiments, the 2-byte counter may be a millisecond timer or a clock-tick counter (i.e., a clock cycle counter) configured to generate a new number corresponding to each successive clock cycle of the processor 307. The instructions stored in the memory device 308, when executed by the processor 307, further cause the processor 307 to obtain or determine the current datetime stamp (i.e., a combination of the calendar date and the time) corresponding to the time at which a data block is stored on the memory device 308. Accordingly, in one or more embodiments, the instructions stored in the memory device 308, when executed by the processor 307, cause the processor 307 to assign a combination of a value (e.g., a number) generated from the 2-byte counter and the current datetime stamp (obtained or generated by the processor 307) to the data blocks as they are stored in the memory device 308. In one or more embodiments, the counter may have any other suitable number of bytes, such as a 1-byte counter or a 3-byte or greater counter, depending upon the number of unique data blocks that are stored per second.

In one or more embodiments, the datetime stamp may have a resolution or a granularity of one second (or approximately one second). Additionally, in one or more embodiments in which the counter is a 2-byte or greater counter, the counter may be able to generate a unique number of values that is at least as large as the number of data blocks that can be stored in the IPG 301 per second. For instance, in one or more embodiments in which the clock cycle of the IPG 301 is approximately 31 micro-seconds (µs) based on a 32 KHz frequency of the clock generator 313, approximately 31,250 clock cycles would occur in one second. Additionally, in one or more embodiments, the IPG 301 takes longer than one clock cycle to write data to the memory device 308 (e.g., EEPROM), and thus no two data blocks can be recorded within one clock cycle. Accordingly, in one or more embodiments, the counter may be a millisecond timer or a 2-byte counter configured to generate 65,536 unique values such that each data block recorded within the resolution of the datetime stamp (e.g., one second) may be assigned a unique identification, which facilitates deduplication of data blocks that are assigned the same unique identification without risk of inadvertently deleting non-duplicated data.

Figure 4:
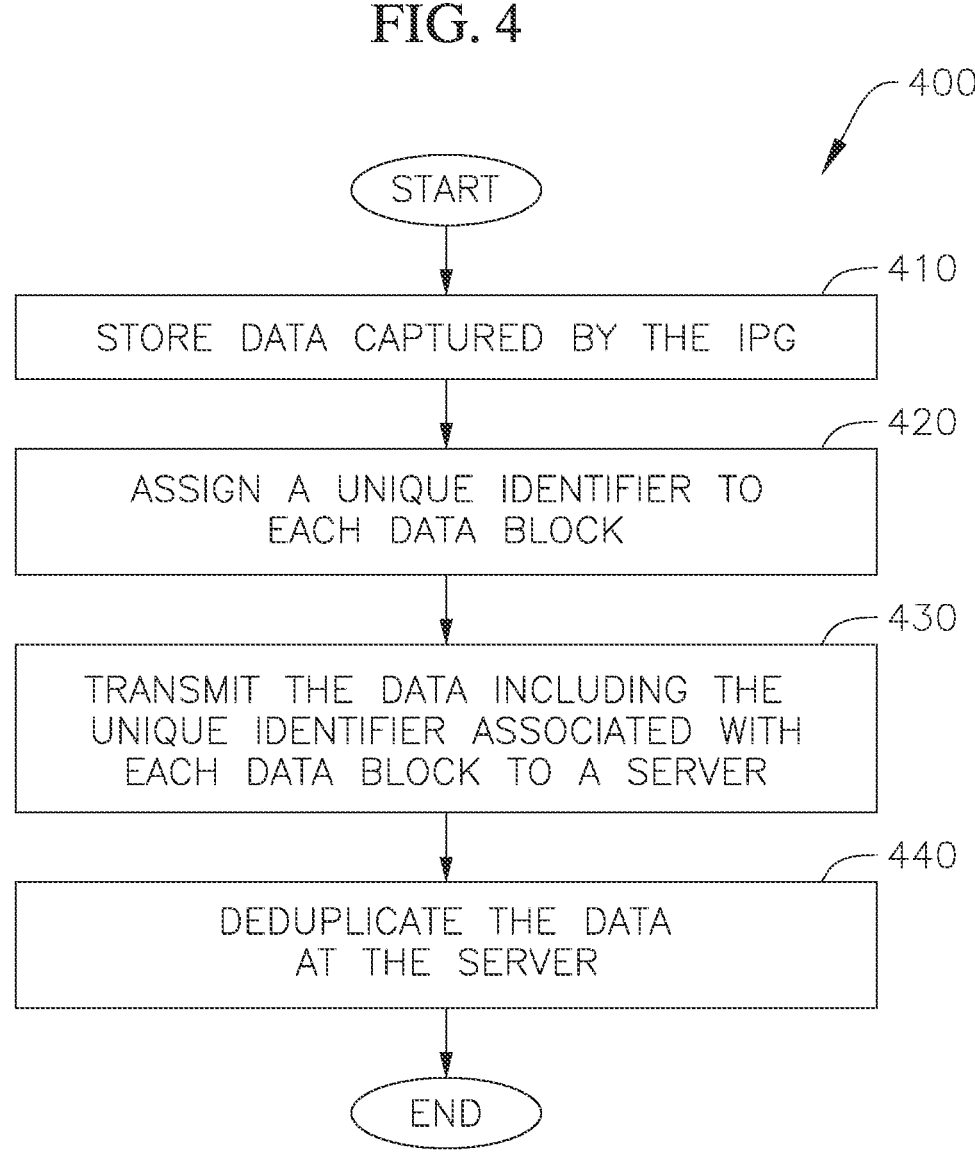
FIG. 4 is a flowchart illustrating tasks of a method of deduplicating data utilizing the therapeutic system of FIGS. 3A-3B according to one embodiment of the present disclosure.

FIG. 4 is a flowchart illustrating tasks of a method 400 of deduplicating data in the system 300 disclosed in FIGS. 3A-3B. In the illustrated embodiment, the method 400 includes a task 410 of storing data, captured or collected by the implantable medical device (e.g., the IPG) 301, in the non-volatile memory 308 of the IPG 301. The data captured or collected by the IPG 301 may include physiological data regarding the patient, therapeutic parameters or settings of the IPG 301, and/or any other relevant data.

In the illustrated embodiment, the method 400 also includes a task 420 of assigning a unique identification to each block of data that was captured or collected by the IPG 301 in task 410. The unique identification assigned in task 420 may be a combination of a datetime stamp corresponding to the date and time at which the data block is captured or collected by the IPG 301 in task 410, and a value generated by a counter. In one or more embodiments, the datetime stamp may have a resolution or a granularity of one second (or approximately one second). Additionally, in one or more embodiments, the counter may be able to generate a unique number of values that is at least as large as the number of data blocks that can be stored in the IPG 301 per second. In one or more embodiments, the counter may be a clock-tick counter (i.e., a clock cycle counter) configured to generate a new number corresponding to each successive clock tick of the clock generator 313 (e.g., the counter may have a resolution or granularity of one clock cycle). For instance, in one or more embodiments in which the clock cycle of the IPG 301 is approximately 31 micro-seconds (μs) based on a 32 KHz crystal frequency of the clock generator 313, approximately 31,250 clock cycles would occur in one second. Additionally, in one or more embodiments, the IPG 301 takes longer than one clock cycle to write data to the memory device 308 (e.g., EEPROM), and thus no two data blocks can be recorded within one clock cycle. Accordingly, in one or more embodiments, the counter may be a milli-second timer or a 2-byte counter configured to generate 65,536 unique values such that each data block recorded within the resolution of the datetime stamp (e.g., one second) may be assigned a unique identification. In one or more embodiments, the counter may have any other suitable number of bytes, such as a 1-byte counter or a 3-byte or greater counter, depending upon the number of unique data blocks that can be recorded within one clock cycle.

In the illustrated embodiment, the method 400 also includes a task 430 of transmitting the data from the IPG 301 to the server 304. In one or more embodiments, the data may be transmitted to the server 304 by the CP device 302 and/or the PR device 303. In one or more embodiments, the data on the IPG 301 may be read by both the CP device 302 and the PR device 303 and then transmitted by both the CP device 302 and the PR device 303 to the server 304.

In the illustrated embodiment, the method 400 also includes a task 440 of deduplicating the data received by the server 304 in task 430 by deleting at least one of two or more data blocks that are associated with the same unique identifier that was assigned to the data blocks in task 420. For instance, in a use case in which both the CP device 302 and the PR device 303 read and transmit the data from the IPG 301 to the server 304 in task 430, two or more data blocks associated with the same unique identifier may have been transmitted to the server in task 430. However, because a unique identifier (i.e., a combination of a datetime stamp and a value from a counter) is assigned to each of the data blocks stored in the non-volatile memory 308 of the IPG 301 in task

420, excess data blocks that are associated with the same unique identifier may be safely deleted by the server 304 without inadvertently deleting non-duplicative data.

Figure 5A:
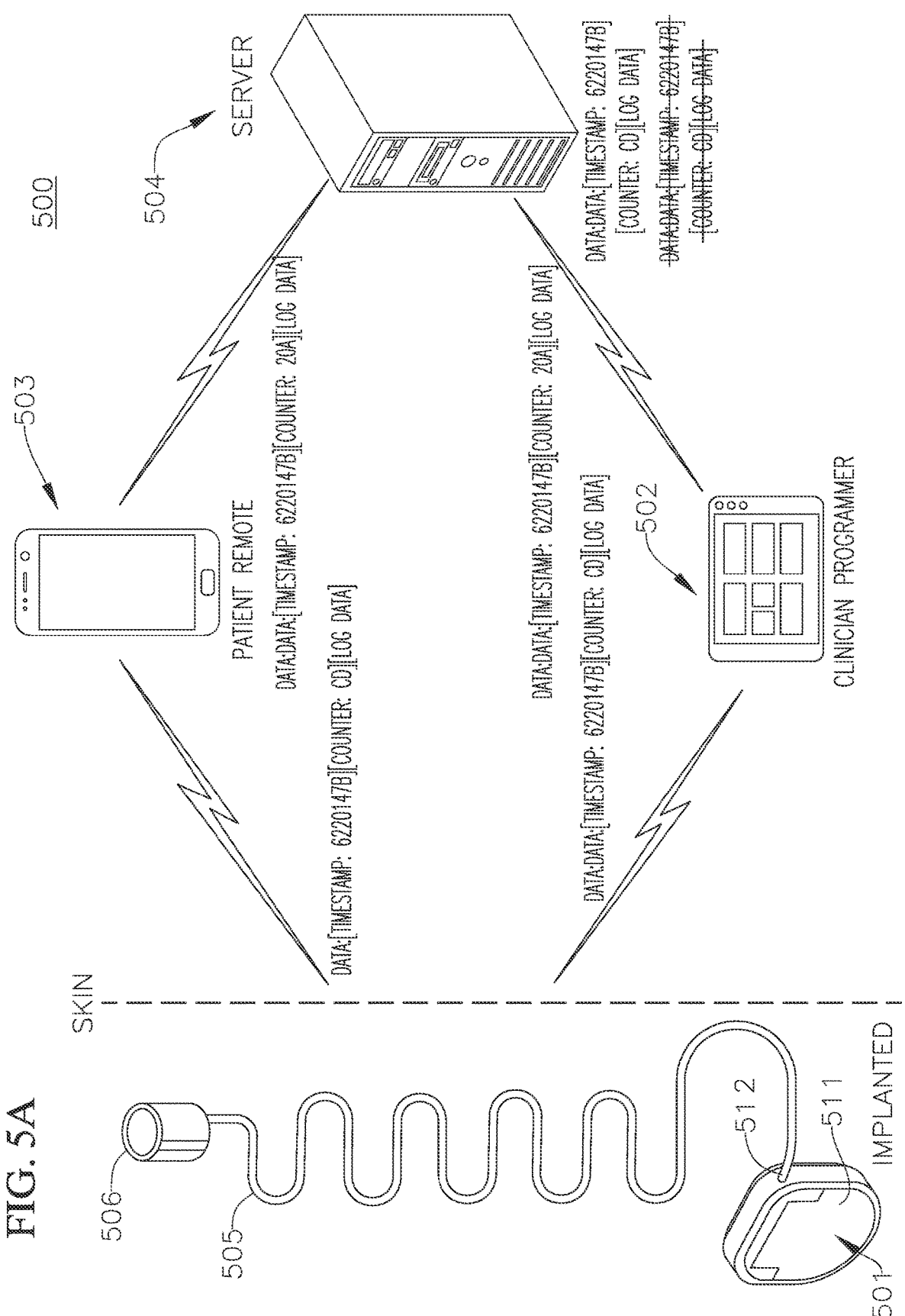
FIG. 5A is a schematic view of a therapeutic system including an implantable pulse generator (IPG), a clinician programmer (CP) device, a patient remote (PR) device, and a server for deduplicating data captured by the IPG according to one embodiment of the present disclosure.

FIG. 5A is a schematic view of a therapeutic system 500 according to one embodiment of the present disclosure. In the illustrated embodiment, the system 500 includes an implantable medical device (e.g., an implantable pulse generator (IPG)) 501 implanted in a patient, a clinician programmer (CP) device 502 electronically coupled to (i.e., in wireless communication with) the IPG 501, a patient remote (PR) device 503 electronically coupled to (i.e., in wireless communication with) the IPG 501, and a server 504 electronically coupled to (i.e., in wireless communication with) the CP device 502 and the PR device 503. The system 500 also includes a plurality of electrical leads 505 connected to the IPG 501. Each of the electrical leads 505 an electrode 506 to periodically deliver an electric current pulse for a variety of therapeutic treatments for the patient, such as neurostimulation, cardiac stimulation, and/or spinal cord stimulation. The IPG 501 and the electrical leads 505 may be implanted in any suitable locations in the patient depending on the therapeutic treatment delivered by the system 500.

Figure 5B:
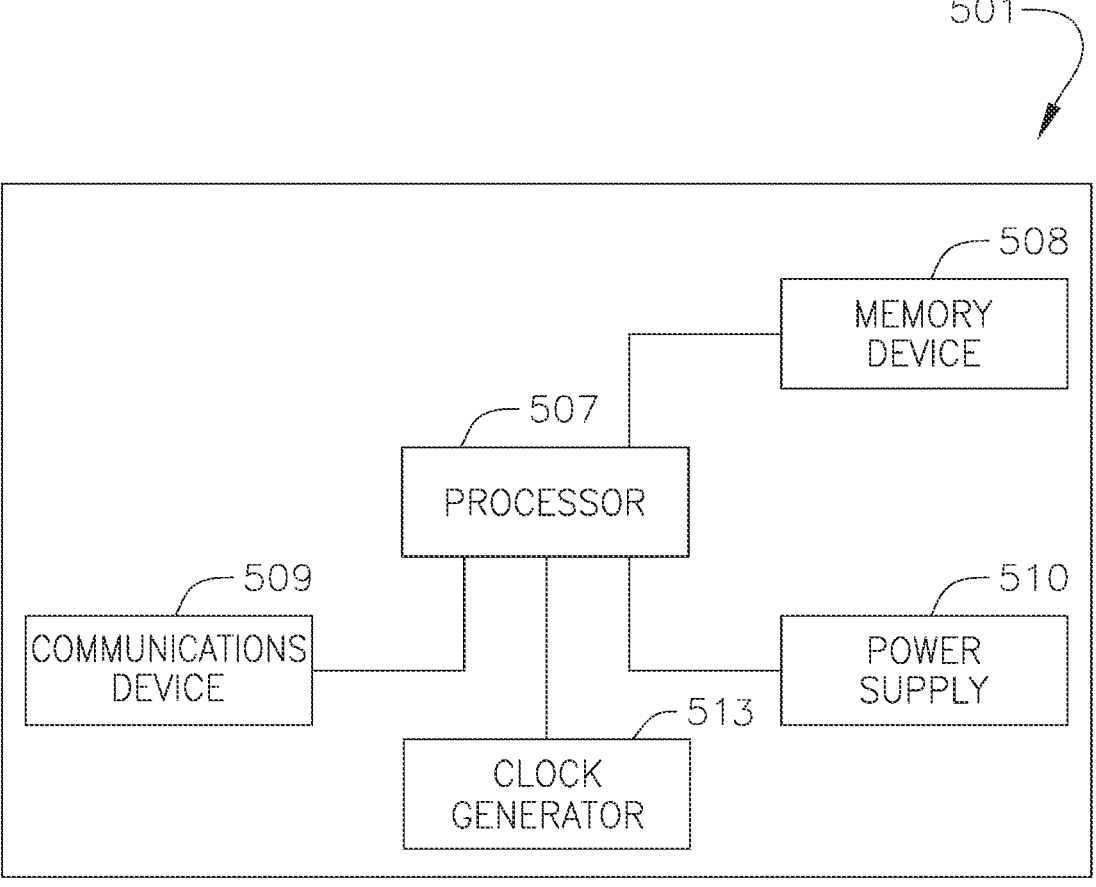
FIG. 5B is a schematic view of the IPG according to the embodiment illustrated in FIG. 5A.

In the embodiment illustrated in FIG. 5B, the implantable medical device (e.g., the IPG) 501 includes a processor 507, a non-volatile memory device 508 (e.g., flash memory, or read-only memory (ROM), such as programmable read-only memory (PROM) or erasable programmable read-only memory (EPROM)), a communications device 509 (e.g., a receiver and a transmitter, or a transceiver), and a power supply 510 (e.g., a primary battery or an inductively chargeable rechargeable battery). The communications device 509 provides wireless communication links through the skin of the patient to the CP device 502 and the PR device 503. Wireless links may include Bluetooth™, Bluetooth Low Energy or other protocols with suitable authentication and encryption to protect patient data. In one or more embodiments, the non-volatile memory device 508, the communications device 509, and the power supply 510 are in communication with each other over the processor 507. Additionally, in the illustrated embodiment, the processor 507, the non-volatile memory device 508, the communications device 509, and the power supply 510 are housed in a housing or a case 511, and proximal end portions of the electrical leads 505 extend through opening(s) 512 in the housing 511 and are connected to the power supply 510, as illustrated in FIG. 5A.

In the illustrated embodiment, the IPG 501 also includes a clock generator 513 (e.g., an oscillator, such as a quartz crystal oscillator, a polycrystalline ceramic oscillator, or other piezoelectric oscillator) configured to generate and provide a clock signal to coordinate write operations to the memory device 508. In one or more embodiments, the clock generator 513 may have a 32 KHz frequency.

The memory device 508 of the IPG 501 is configured to store various data about the patient (e.g., physiological data regarding the patient, therapeutic parameters or settings of the IPG 501, and/or any other relevant data), and the CP device 502 and the PR device 503 are each configured to periodically read and transmit the data stored on the memory device 508 of the IPG 501 to the server 504, which enables remote monitoring of the system 500.

In one or more embodiments, the memory device 508 of the IPG 501 includes instructions (e.g., computer-readable code) stored therein, which, when executed by the processor 507, cause the IPG 501 to generate and assign a unique identifier to each data block that is stored in the memory device 508 of the IPG 501. Assigning a unique identifier to each data block as it is saved on the memory device 508 enables the data received by the server 504 from the CP device 502 and the PR device 503 to be deduplicated (e.g., if the same data is sent to the server 504 both by the CP device 502 and the PR device 503).

In the illustrated embodiment, the unique identifier is a combination of a value (e.g., a number) and a datetime stamp. In the illustrated embodiments, the instructions stored in the memory device 508 include a 1-byte counter configured to generate 256 (i.e., $2^8 = 256$) unique values. The instructions stored in the memory device 508, when executed by the processor 507, further cause the processor 507 to obtain or determine the current datetime stamp (i.e., a combination of the calendar date and the time) corresponding to the time at which a data block is stored on the memory device 508. Accordingly, in one or more embodiments, the instructions stored in the memory device 508, when executed by the processor 507, cause the processor 507 to assign a combination of a value (e.g., a number) generated from the 1-byte counter and the current datetime stamp (obtained or generated by the processor 507) to the data blocks as they are stored in the memory device 508.

In one or more embodiments, the datetime stamp may have a resolution or a granularity of one second (or approximately one second). Additionally, in one or more embodiments, the counter may be able to generate a unique number of values that is at least as large as the number of data blocks that can be stored in the IPG 501 per second. For instance, in one or more embodiments, the IPG 501 is configured to store up to 255 data blocks in the non-volatile memory 508 per second and the 1-byte counter is configured to generate 256 (i.e., $2^8 = 256$) unique values such that each data block recorded within the resolution of the datetime stamp (e.g., one second) may be assigned a unique identification, which facilitates deduplication of data blocks that are assigned the same unique identification without risk of inadvertently deleting non-duplicated data. In one or more embodiments, the counter may have any other suitable number of bytes, such as a 1-byte counter or a 3-byte or greater counter, depending upon the number of unique data blocks that are stored per second.

Figure 6:
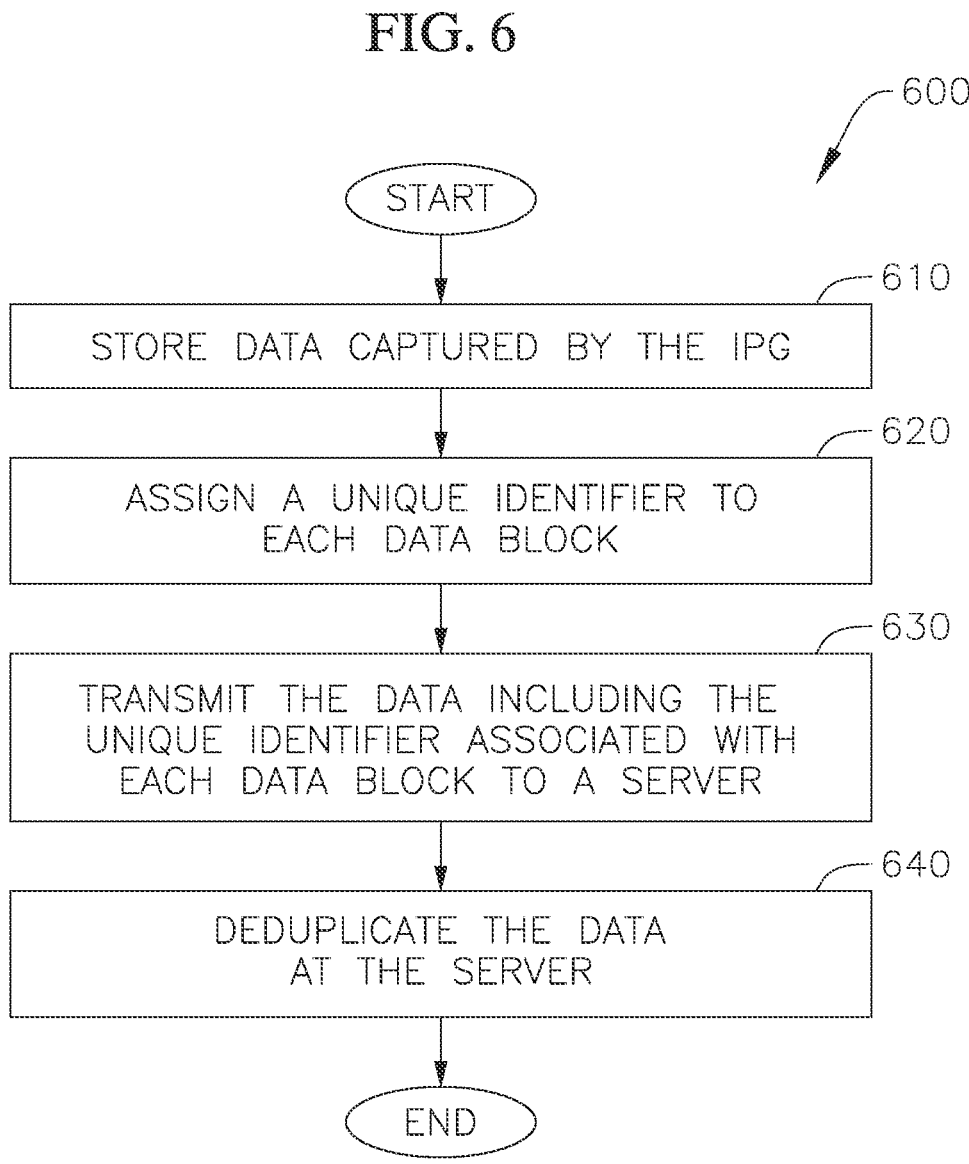
FIG. 6 is a flowchart illustrating tasks of a method of deduplicating data utilizing the therapeutic system of FIGS. 5A-5B according to one embodiment of the present disclosure.

FIG. 6 is a flowchart illustrating tasks of a method 600 of deduplicating data on the system 500 disclosed in FIGS. 5A-5B. In the illustrated embodiment, the method 600 includes a task 610 of storing data, captured or collected by the implantable medical device (e.g., the IPG) 501, in the non-volatile memory 508 of the IPG 501. The non-volatile memory 508 of the IPG 501 may be any suitable type or kind of memory, such as electrically erasable programmable read-only memory (EEPROM). The data captured or collected by the IPG 501 may include physiological data regarding the patient, therapeutic parameters or settings of the IPG 501, and/or any other relevant data.

In the illustrated embodiment, the method 600 also includes a task 620 of assigning a unique identification to each block of data that was captured or collected by the IPG 501 in task 610. The unique identification assigned in task 620 may be a combination of a datetime stamp (corresponding to the date and time at which the data block is stored by the IPG 501 in task 610) and a value generated by a counter. In one or more embodiments, the datetime stamp may have a resolution or a granularity of one second. Additionally, in one or more embodiments, the counter may be able to generate a unique number of values that is at least as large as the number of data blocks that can be stored in the IPG 501 per second. For instance, in one or more embodiments in which the IPG 501 is configured to store up to 255 data blocks in the non-volatile memory 508 per second, the counter may be a 1-byte counter configured to generate 256 (i.e., $2^8 = 256$) unique values such that each data block recorded within the resolution of the datetime stamp (e.g., one second) may be assigned a unique identification. Accordingly, in task 620, a unique number generated by the 1-byte counter may be assigned to each data block stored by the IPG 501 per second. In one or more embodiments, the counter may reset when the datetime stamp changes (e.g., the counter may reset every second when the datetime stamp has a resolution of one second). In one or more embodiments, the counter may not reset when the datetime stamp changes. In one or more embodiments, the counter may have any other suitable number of bytes, such as a 1-byte counter or a 3-byte or greater counter, depending upon the number of unique data blocks that are stored per second such that the counter can generate a unique number of values that is at least as large as the number of data blocks that can be stored in the IPG 501 per second.

In the illustrated embodiment, the method 600 also includes a task 630 of transmitting the data from the IPG 501 to the server 504. In one or more embodiments, the data may be transmitted to the server 504 by the CP device 502 and/or the PR device 503. In one or more embodiments, the data on the IPG 501 may be read by both the CP device 502 and the PR device 503 and then transmitted by both the CP device 502 and the PR device 503 to the server 504.

In the illustrated embodiment, the method 600 also includes a task 640 of deduplicating the data received by the server 504 in task 630 by deleting at least one of two or more data blocks that are associated with the same unique identifier that was assigned to the data blocks in task 620. For instance, in a use case in which both the CP device 502 and the PR device 503 read and transmit the data from the IPG 501 to the server 504 in task 630, two or more data blocks associated with the same unique identifier may have been transmitted to the server in task 630. However, because a unique identifier (e.g., a combination of a datetime stamp and a value from a counter, such as a 1-byte counter) is assigned to each of the data blocks stored in the non-volatile memory 508 of the IPG 501 in task 620, excess data blocks that are associated with the same unique identifier may be safely deleted by the server 504 without inadvertently deleting non-duplicative data.

The implantable medical device (e.g., the implantable pulse generator (IPG)) and/or any other relevant devices or components according to embodiments of the present invention described herein may be implemented utilizing any suitable hardware, firmware (e.g. an application-specific integrated circuit), software, or a combination of software, firmware, and hardware. For example, the various components of the device may be formed on one integrated circuit (IC) chip or on separate IC chips. Further, the various components of the device may be implemented on a flexible printed circuit film, a tape carrier package (TCP), a printed circuit board (PCB), or formed on one substrate. Further, the various components of the device may be a process or thread, running on one or more processors, in one or more computing devices, executing computer program instructions and interacting with other system components for performing the various functionalities described herein. The computer program instructions are stored in a memory which may be implemented in a computing device using a standard memory device, such as, for example, a random access memory (RAM). The computer program instructions may also be stored in other non-transitory computer readable media such as, for example, a CD-ROM, flash drive, or the like. Also, a person of skill in the art should recognize that the functionality of various computing devices may be combined or integrated into a single computing device, or the functionality of a particular computing device may be distributed across one or more other computing devices without departing from the scope of the exemplary embodiments of the present invention.

Although some embodiments of the present disclosure are disclosed herein, the present disclosure is not limited thereto, and the scope of the present disclosure is defined by the appended claims and equivalents thereof.

What is claimed is:

1. A method of deduplicating data collected by an implantable medical device, the method comprising:

storing data, captured by the implantable medical device, in a non-volatile memory device of the implantable medical device;

assigning a unique number, generated from a random number generator or a counter, to each data block of the data; and deduplicating the data by deleting at least one of two or more data blocks being associated with a same unique number.

2. The method of claim 1, wherein the random number generator is a 4-byte random number generator, and wherein the counter is a 4-byte counter.

3. The method of claim 2, wherein the assigning the unique number comprises:

generating a random number or a pseudo-random number from the 4-byte random number generator by supplying a current datetime as a seed for the 4-byte random number generator; and assigning the random number or the pseudo-random number to each data block of the data.

4. The method of claim 2, wherein the assigning the unique number comprises generating a number from the 4-byte counter.

5. The method of claim 1, wherein the implantable medical device is an implantable pulse generator, the method further comprising:

transmitting the data from the implantable pulse generator to each of a clinician programmer device and a patient remote device; and transmitting the data from each of the clinician programmer device and the patient remote device to a server, wherein the server performs the deduplicating of the data.

* * * * *